United States Patent [19]

Nagai et al.

[11] 4,350,643

[45] Sep. 21, 1982

[54] PROCESS FOR PRODUCING 2,3-DIHALOPROPIONITRILE

[75] Inventors: Shosuke Nagai, Yokohama; Toshio Kato, Kawasaki; Chojiro H. Iguchi; Nobuyuki Kawashima, both of Kamakura; Ryuichi Mita, Kawasaki; Akihiro Yamaguchi, Kamakura; Takao Takano, Fujisawa, all of Japan

[73] Assignee: Mitsui Toatsu Chemicals, Inc., Tokyo, Japan

[21] Appl. No.: 215,818

[22] Filed: Dec. 12, 1980

[30] Foreign Application Priority Data

Dec. 18, 1979 [JP] Japan .............................. 54-163586
Jan. 23, 1980 [JP] Japan .............................. 55-5864

[51] Int. Cl.$^3$ ................. C07C 120/00; C07C 121/16
[52] U.S. Cl. .............................................. 260/465.7
[58] Field of Search ..................... 260/465.7; 570/247

[56] References Cited

U.S. PATENT DOCUMENTS

| | | | |
|---|---|---|---|
| 2,231,360 | 2/1941 | D'Tanni ................... | 260/465.7 X |
| 2,231,363 | 2/1941 | Long ......................... | 260/465.7 |
| 2,298,739 | 10/1942 | Lichty et al. ............ | 260/465.7 |
| 2,390,470 | 12/1945 | Sumner .................... | 260/465.7 X |
| 2,710,304 | 6/1955 | Opfermann .............. | 260/465.7 X |
| 3,401,105 | 9/1968 | Anyos et al. ............ | 204/153 |
| 3,716,591 | 2/1973 | Brady ....................... | 570/247 |
| 3,736,346 | 5/1973 | Tsurushima et al. .... | 260/465.7 X |
| 3,739,010 | 6/1973 | Suzuki et al. ............ | 260/465.7 |

FOREIGN PATENT DOCUMENTS

842193 6/1952 Fed. Rep. of Germany.
6612041 2/1967 Netherlands.

OTHER PUBLICATIONS

C. Moureu and R. L. Brown, Bull. Soc. Chim. Fr., vol. 27, (1920), pp. 901–903.
L. Petit and P. Touratier, Bull. Soc. Chim. Fr., vol. 3, (1968), pp. 1136 and 1138.
M. A. Naylor and A. W. Anderson, J. Am. Chem. Soc., vol. 75, (1953), pp. 5392 and 5394.
H. Brockmann and H. Musso, Chem. Ber., vol. 87, (1954), pp. 580, 590 and 591.
A. V. Bombrovskii, Zhur. Obschch. Khim., vol. 24, (1954), pp. 610, 611, 612, 613.
H. Brintzinger, K. Pfannstiel and H. Koddebusch, Angew. Chem., vol. A(60), (1948), pp. 311–312.
W. H. Jura and R. J. Gaul, J. Am. Chem. Soc., vol. 80, pp. 5402 and 5403.
S. S. Ivanov and M. M. Koton, Zhur. Obshch. Khim., vol. 28, p. 139, (1958).
M. A. Askarov, K. A. Avlyanov and A. B. Alovitdinov, Uzebeksk. Khim. Zh., vol. 7(5), (1963), pp. 50–51.
Chem. Abst., 61, 10623a, (1964).
Chem. Abst., 56, 5825c, (1962).
W. W. Moyer, Jr., T. Anyos and D. L. Dennis, Jr., J. Org. Chem., vol. 31 (4), p. 1094, (1966).
N. B. Lorette, J. Org. Chem., vol. 26, p. 2324, (1961).

Primary Examiner—Joseph Paul Brust
Attorney, Agent, or Firm—Fisher, Christen & Sabol

[57] ABSTRACT

A process for producing a 2,3-dihalopropionitrile is provided which comprises directly halogenating acrylonitrile with a halogenating agent in the presence of a carbonate, hydrogen carbonate or hydrogen phosphate of an alkali or alkaline earth metal and in the absence of positive irradiation of light.

11 Claims, No Drawings

PROCESS FOR PRODUCING 2,3-DIHALOPROPIONITRILE

BACKGROUND OF THIS INVENTION

1. Field of this Invention

This invention relates to a process for producing a 2,3-dihalopropionitrile which is a compound useful as a material for producing polymeric compounds or biologically active substances such as amino acids, agricultural chemicals and pharmaceuticals.

2. Prior Art

Conventional methods for producing 2,3-dihalopropionitriles by halogenation of acrylonitrile are carried out in various modes, for example, in the absence of a catalyst, or in the presence of a catalyst, or by utilizing a photo-radical reaction.

Various methods have been proposed for direct halogenation of acrylonitrile in the absence of a catalyst. For example, U.S. Pat. No. 2,231,360 and West German Patent No. 842,193 disclose a method for producing 2,3-dichloropropionitrile by introducing a chlorine gas into acrylonitrile in the presence of water. This method, however, is not commercially feasible because the yield of the product is as low as 26 to 29%. U.S. Pat. No. 2,298,739; C. Moureu and R. L. Brown, Bull. Soc. Chim. Fr., vol. 27, page 901, 1920; and L. Petit and P. Touratier, Bull. Soc. Chim. Fr., vol. 3, page 1136, 1968, disclose a method for producing 2,3-dihalopropionitriles by directly halogenating acrylonitrile with halogenating agents in chloroform or carbon tetrachloride as a solvent. This method, however, is not suitable for commercial practice because it requires recovery of the solvent. M. A. Naylor and A. W. Anderson, J. Am. Chem. Soc., vol. 75, page 5392, 1953; H. Brockmann and H. Musso, Chem. Ber., vol. 87, page 590, 1954; and U.S. Pat. No. 2,710,304 disclose a method for producing 2,3-dibromopropionitrile by the direct action of bromine on acrylonitrile. According to this method, the yield is as low as 70 to 89%. Elsewhere, A. V. Dombrovskii, Zhur. Obshch. Khim., vol. 24, page 610, 1954, discloses dibromination of acrylonitrile with dioxane dibromide as a halogenating agent. This method, however, is not commercially feasible because the use of the special halogenating agent adds to the cost of production and the yield of the product is as low as 50 to 55%.

Methods using catalysts have also been proposed. For example, H. Brintzinger, K. Pfannstiel and H. Koddebusch, Angew. Chem., vol. A(60), page 311, 1948; W. H. Jura and R. J. Gaul, J. Am. Chem. Soc., vol. 80, page 5402, 1958; S. S. Ivanov and M. M. Koton, Zhur. Obshch. Khim., vol. 28, page 139, 1958; and N. O. Pastushak, A. V. Dombrovskii and L. I. Pogovik, Zhur. Obshch. Khim., vol. 34 (7), page 2243, 1964, disclose halogenation of acrylonitrile in the presence of a pyridine catalyst. According to this method, the reaction mixture obtained by the reaction should be washed with water in order to remove the pyridine catalyst. Consequently, a part of the resultant 2,3-dihalopropionitrile dissolves in water together with the unreacted acrylonitrile to cause a decrease in the yield of the desired product. It also gives rise to a problem of treating the waste water. A method of halogenating acrylonitrile in the presence of an N,N-dimethyl formamide catalyst is disclosed in I. P. Losev, O. V. Smirnova and L. M. Lutsenko, Trudy Moskov. Khim. Tekhnol. Inst. im. D. I. Mendeleeva, vol. 29, page 17, 1959, and M. A. Askarov, K. A. Avlyanov and A. B. Alovitdinov, Uzbeksk. Khim. Zh., vol. 7(5), page 50, 1963. In this method, 2,3-dichloropropionitrile is obtained in a yield of 92.3% by adding 3% by weight of N,N-dimethyl formamide to acrylonitrile and chlorinating it. The inventors of the present application have traced this method and found that when the amount of N,N-dimethyl formamide is 3% by weight, the conversion of acrylonitrile is as low as 40 to 45%. Hence, this method is not commercially viable.

Production of a 2,3-dihalopropionitrile by photoradical reaction is disclosed, for example, in W. W. Moyer Jr., T. Anyos and J. L. Dennis Jr., J. Org. Chem., vol. 31 (4), page 1094, 1966, and Dutch Laid-Open Patent No. 6,612,041. According to this technique, the 2,3-dihalopropionitrile is obtained from acrylonitrile by photo-radical reaction using an alkali metal hydrogen phosphate as an ionic reaction inhibitor. U.S. Pat. No. 2,390,470 and N. B. Lorette, J. Org. Chem., vol. 26, page 2324, 1961, disclose a method in which photochlorination of acrylonitrile is carried out in the absence of an additive. According to these methods involving photo-radical reaction, the yield of the 2,3-dihalopropionitrile is low, and the reaction apparatus becomes complex because photo-reaction is carried out therein. Hence, for commercial practice, these methods give rise to many problems.

BROAD DESCRIPTION OF THIS INVENTION

It is an object of this invention therefore to provide a commercially advantageous process for producing a 2,3-dihalogenopropionitrile.

As a result of extensive investigation, we now provide a process for producing a 2,3-dihalogenopropionitrile which comprises halogenating acrylonitrile with a halogenating agent in the presence of a carbonate, hydrogen carbonate or hydrogen phosphate of an alkali or alkaline earth metal as a halogenating catalyst and in the substantial absence of light.

The halogenation reaction in the present invention is not a photochemical reaction, and therefore does not require a special reaction apparatus. Moreover, since it gives the 2,3-dihalopropionitrile in a quantitative yield without substantially forming by-products, the process of this invention is an excellent commercial process.

In the process of this invention, the catalyst used can be separated easily from the reaction product by an operation such as mere filtration because it is an inorganic salt insoluble in the reaction mixture. Thus, the process of this invention is superior as a commercial process to the known methods.

The halogenating agent used in the process of this invention includes bromine, chlorine, iodine, and fuorine. Generally, chlorine or bromine is used.

Examples of the carbonate or hydrogen carbonate of an alkali or alkaline earth metal include carbonates or hydrogen carbonates of sodium, potassium, lithium, magnesium and calcium. Usually, sodium carbonate, potassium carbonate, sodium hydrogen carbonate and potassium hydrogen carbonate are used.

Examples of the alkali or alkaline earth metal hydrogen phosphate are dipotassium hydrogen phosphate, disodium hydrogen phosphate and calcium hydrogen phosphate.

The above inorganic salts may be used singly or as a mixture of two or more.

The catalyst remaining in the reaction solution may be recovered by extraction with water because it is an inorganic salt and is insoluble in the reaction solution. But it can be easily recovered by simple filtration or decantation. When the alkali or alkaline earth metal hydrogen phosphate is used as the catalyst, the recovered catalyst can be easily regenerated by treatment with a strong alkali.

The amount of the alkali or alkaline earth metal carbonate, hydrogen carbonate or hydrogen phosphate as a catalyst is 0.05 to 2 moles per mole of acrylonitrile. For practical purposes, amounts of 0.05 to 1.0 mole are sufficient.

Halogenation of acrylonitrile in the process of this invention is usually performed in the absence of a solvent. But, if desired, it may be performed in the presence of organic solvents usually employed in halogenation, such as chloroform or carbon tetrachloride.

The process of this invention is usually practised in a substantially anhydrous condition. But even when a catalyst containing water of crystallization or acrylonitrile of industrial grade containing some water is used, no practical problem arises.

Preferably, halogenation of acrylonitrile and optional distillation of the reaction product in the process of this invention are performed usually in the presence of a polymerization inhibitor. Examples of the polymerization inhibitor are hydroquinone, phenyl-betanaphthylamine, diphenyl-p-phenylenediamine, tert.-butyl catechol, picric acid, phenothiazine, sulfur, sulfur compounds, copper and copper compounds. The amount of the polymerization inhibitor is 5 to 100 ppm based on acrylonitrile, and for practical purposes, amounts of 20 to 60 ppm are sufficient.

Halogenation is usually performed under atmospheric pressure, but may be carried out if desired under elevated or reduced pressure without any consequent trouble. The reaction temperature is $-70°$ to $110°$ C. and the reaction time is 2 to 20 hours. In industrial practice, the reaction is preferably carried out at $-20°$ to $40°$ C. for 4 to 10 hours.

In the process of this invention, the halogenation reaction does not require any positive irradiation of light, and therefore the reaction proceeds in the substantial absence of light. If desired, however, it may be carried out in the presence of scattering light which has been transmitted through glass.

The end point of the reaction can be easily determined by quantitatively analyzing the reaction mixture by gas chromatography, or by measuring a weight increase of the reaction mixture, or by measuring the specific gravity of the reaction mixture. Gas chromatographic analysis of the reaction mixture is carried out by packing a filler (Porapak Q, 80-100 mesh) into a column having a diameter of 3 mm and a length of 1 m, and using nitrogen as a carrier gas while maintaining the temperature of the column at 190° C.

In the process of this invention, the halogenation reaction and the optional distillation under reduced pressure of the 2,3-dihalopropionitrile are preferably carried out in an oxygen-free atmosphere. In actual operations, the reaction and the distillation are carried out in an atmosphere of an inert gas such as nitrogen gas or carbon dioxide gas.

The material of which the reaction apparatus used in the process of this invention is made may be any material which does not undergo corrosive attack of the halogen, hydrogen halide and the product. Generally, it is glass or a material coated with a vitreous substance.

After the reaction, the reaction mixture is subjected to filtration, decantation or extraction with water to remove the catalyst. Distillation of the residue under reduced pressure quantitatively gives a 2,3-dihalopropionitrile. Needless to say, purification after distillation gives the 2,3-dihalopropionitrile in a higher purity.

Since scarcely any by-product forms in the process of this invention, the reaction mixture as obtained after the reaction can be used as a starting material for various reactions starting from 2,3-dihalonitrile if only the catalyst is removed from it by filtration or water extraction.

DETAILED DESCRIPTION OF THE INVENTION

The following Examples more specifically illustrate the process of this invention.

EXAMPLE 1

A 300 ml brown flask equipped with a thermometer, a stirrer, a glass ball filter-fitted gas-blowing tube and reflux condenser was charged with 53.1 g (1.0 mole) of acrylonitrile containing 40 ppm of hydroquinone and 12.7 g (0.12 mole) of anhydrous sodium carbonate. While purging the inside of the reactor with nitrogen gas, the mixture was cooled to 5° C. with ice-water. When the temperature of the inside of the flask reached 5° C., chlorine gas was introduced into the reaction solution at a rate of 0.23 to 0.24 g/min. through the glass ball filter with stirring. The reaction was continued at 5° to 10° C. for about 5 hours.

The reaction mixture was analyzed by gas chromatography, and the time when the starting acrylonitrile in the reaction mixture remained only in a trace amount was regarded as the end point of the reaction.

After the reaction, the introduction of chlorine gas was stopped, and nitrogen gas was blown into the reaction solution to remove chlorine gas dissolved in it. The reaction solution was filtered at room temperature to separate the sodium carbonate catalyst by filtration. Distillation under reduced pressure of 122.7 g of the filtrate (colorless clear liquid) in a nitrogen stream gave 1.6 g (yield of 2.2% based on acrylonitrile) as a first fraction boiling at 43° to 45° C. (150 mmHg) and 119.7 g (yield of 96.5% based on acrylonitrile) of 2,3-dichloropropionitrile as a second fraction boiling at 62° to 63° C. (150 mmHg).

EXAMPLE 2

Acrylonitrile (53.1 g) was chlorinated in the same way as in Example 1 at $-10°$ to $-5°$ C. in the presence of 12.6 g (0.15 mole) of anhydrous sodium hydrogen carbonate. After the reaction, the reaction mixture was subjected to dechlorination, filtration and vacuum distillation by the same operations as in Example 1 to afford 120.5 g (yield of 97.2% based on acrylonitrile) of 2,3-dichloropropionitrile. Formation of 2-chloroacrylonitrile was not observed.

EXAMPLE 3

By the same operation as in Example 1, 53.1 g of acrylonitrile and 13.8 g (1.0 mole) of anhydrous potassium carbonate were charged into a flask, and 159.8 g (1.0 mole) of bromine was added dropwise at 0° to 5° C. for 3 hours. The reaction was performed at this temperature for 2 hours. After the reaction, the reaction solution was washed three times with 100 ml of water, dehydrated over anhydrous magnesium sulfate, and distilled under reduced pressure. There was obtained 209.3 g (yield of 98.3% based on acrylonitrile) of 2,3-dibromopropionitrile at 78°–80° C. (14 mmHg).

EXAMPLE 4

In the same way as in Example 1, 53.1 g of acrylonitrile was chlorinated at 20° to 25° C. in the presence of 20.0 g (0.2 mole) of anhydrous calcium carbonate. When the weight of the reaction solution reached 124 g which was the weight showing that 2,3-dichloropropionitrile was formed in a calculated amount, the reaction was stopped. Chlorine dissolved in the reaction solution was removed with nitrogen. The weight of the reaction product at this time was 116.6 g. The catalyst was separated by filtration, and the reaction solution was distilled under reduced pressure to afford 0.7 g of acrylonitrile as a first fraction boiling at 23° C. (100 mmHg), 3.1 g (yield of 4.2% based on acrylonitrile) of 2-chloroacrylonitrile as a second fraction boiling at 43°–44° C. (150 mmHg), and 112.3 g (yield of 90.5% based on acrylonitrile) of 2,3-dichloropropionitrile as a third fraction boiling at 62°–63° C. (13 mmHg).

EXAMPLE 5

The same flask as used in Example 1 was charged with 53.1 g of acrylonitrile containing 0.2% by weight of hydroquinone, and 17.4 g of disodium hydrogen phosphate. The inside of the reactor was purged with nitrogen, and chlorine gas at 10° to 15° C. was blown into the flask through a glass ball filter. Chlorine was blown into it at this temperature for 5 to 6 hours. After confirming that the specific gravity of the solution ($d_{20}$) reached 1.37, blowing of chlorine was stopped. The reaction solution was stirred for 1 hour to substitute nitrogen gas for chlorine dissolved in it. The reaction product was analyzed by gas chromatography, and found to contain 98.0% of 2,3-dichloropropionitrile, 1.6% of 2-chloroacrylonitrile and 0.3% of unreacted acrylonitrile. The reaction solution was filtered to remove the catalyst, and the residue was distilled in a brown glass distillation device at a boiling point of 62° to 63° C. under a pressure of 13 mmHg to afford 120.0 g (yield of 96.8% based on acrylonitrile: specific gravity of $d_{20}$ 1.35) of 2,3-dichloropropionitrile.

EXAMPLE 6

In the same way as in Example 1, 53.1 g of acrylonitrile was chlorinated in the presence of 17.4 g of dipotassium hydrogen phosphate. While maintaining the reaction temperature at 0° to 5° C., chlorine gas was blown into the reaction system for 6 to 7 hours. After confirming by gas chromatography that the reaction reached an end point, the catalyst was separated from the reaction mixture by filtration. There was obtained 2,3-dichloropropionitrile in a yield of 99.7%. As a by-product, 0.3% of 2-chloroacrylonitrile was formed.

EXAMPLE 7

In the same way as in Example 1, a flask was charged with 53.1 g of acrylonitrile and 71.6 g of disodium hydrogen phosphate dodecahydrate ($Na_2HPO_4.12H_2O$). While maintaining the reaction temperature at 20° to 25° C., 160 g of bromine was added dropwise over the course of 5 hours. The mixture was stirred at this temperature for 1 to 2 hours, and 100 g of water was added to dissolve $Na_2HPO_4.12H_2O$. The reaction mixture was separated from the aqueous layer, dehydrated over anhydrous sodium sulfate, and distilled at 90° to 91° C. under a reduced pressure of 15 mmHg to afford 206.5 g (yield of 97.0% based on acrylonitrile; specific gravity of $d_{20}$ 2.11) of 2,3-dibromopropionitrile.

The aqueous layer was heated with 50 g of a 45% aqueous solution of sodium hydroxide and concentrated under reduced pressure. The precipitate was separated by filtration and dried. The dried product could again be used as a catalyst in the next reaction.

EXAMPLE 8

In the same way as in Example 1, a flask was charged with 53.1 g of acrylonitrile, 8.5 g of disodium hydrogen phosphate and 10.5 g of dipotassium hydrogen phosphate. In a dark place, 160 g of bromine was added dropwise to the flask at 30° to 40° C. over the course of 5 hours. After the addition, the mixture was stirred at this temperature for 1 hour, and then the catalyst was separated by filtration. Gas-chromatographic analysis showed that the product consisted of 99.2% of 2,3-dibromopropionitrile, 0.7% of 2-bromoacrylonitrile and a trace of the unreacted acrylonitrile.

What is claimed is:

1. A process for producing a 2,3-dihalopropionitrile which comprises halogenating acrylonitrile with a halogenating agent in the presence of, as a catalyst, a carbonate of an alkali metal or an alkaline earth metal, or a hydrogen carbonate of an alkali metal or an alkaline earth metal, or a hydrogen phosphate of an alkali metal or an alkaline earth metal, the halogenating agent being chlorine or bromine, the halogenation being carried out in substantially the absence of irradiation by light, and the halogenation being carried out at −70° to 110° C.

2. The process of claim 1 wherein the catalyst is sodium carbonate or potassium carbonate.

3. The process of claim 1 wherein the catalyst is sodium hydrogen carbonate or potassium hydrogen carbonate.

4. The process of claim 1 wherein the catalyst is disodium hydrogen phosphate or dipotassium hydrogen phosphate.

5. The process of claim 1 wherein the catalyst is calcium hydrogen phosphate.

6. The process of claim 1 wherein the amount of the catalyst is from 0.05 to 2 moles per mole of acrylonitrile.

7. The process of claim 1 wherein the halogenation is carried out in the absence of a solvent.

8. The process of claim 1 wherein the halogenation is carried out in a halogenated aliphatic hydrocarbon as a solvent.

9. The process of claim 1 wherein the halogenation is carried out at −20° C. to 40° C.

10. The process of claim 1 wherein the halogenation is carried out in an atmosphere of an inert gas.

11. A process for producing a 2,3-dihalopropionitrile which comprises halogenating acrylonitrile with a halogenating agent in the presence of, as a catalyst, a carbonate of an alkali metal or an alkaline earth metal, or a hydrogen carbonate of an alkali metal or an alkaline earth metal, or a hydrogen phosphate of an alkali metal or an alkaline earth metal, the halogenating agent being chlorine or bromine, the halogenation being carried out in substantially the absence of irradiation by light, the halogenation being carried out at −70° to 110° C., the halogenation being conducted under an atmosphere of an inert gas.

* * * * *